US012667668B2

(12) United States Patent
Lizari Illarramendi et al.

(10) Patent No.: US 12,667,668 B2
(45) Date of Patent: Jun. 30, 2026

(54) MACHINE FOR THE PREPARATION OF MEDICAL PRODUCT WITH DEVICE FOR LOADING SYRINGES OF MEDICAL PRODUCT

(71) Applicant: KIRO GRIFOLS, S.L., Arrasate (ES)

(72) Inventors: Borja Lizari Illarramendi, Arrasate (ES); Naiara Telleria Garay, Arrasate (ES); Patxi Urtzelai Aranbarri, Arrasate (ES); Jose Ignacio Andres Pineda, Arrasate (ES); Amaia Ilzarbe Andres, Arrasate (ES)

(73) Assignee: Kiro Grifols, S.L., Arrasate (ES)

( * ) Notice: Subject to any disclaimer, the term of this patent is extended or adjusted under 35 U.S.C. 154(b) by 580 days.

(21) Appl. No.: 18/320,914

(22) Filed: May 19, 2023

(65) Prior Publication Data
US 2024/0001040 A1     Jan. 4, 2024

(30) Foreign Application Priority Data
Jul. 1, 2022     (EP) .................................... 22382633

(51) Int. Cl.
*B65D 85/42*     (2006.01)
*A61M 5/20*     (2006.01)

(52) U.S. Cl.
CPC ................................. *A61M 5/2033* (2013.01)

(58) Field of Classification Search
CPC ......... B65B 23/22; B65B 35/16; B65B 35/36; B65B 3/003; B65D 85/42; A61J 1/1493; A61M 5/008
See application file for complete search history.

(56) References Cited

U.S. PATENT DOCUMENTS

| | | | |
|---|---|---|---|
| 5,934,859 A | 8/1999 | Goetzelmann | |
| 6,123,205 A | 9/2000 | Dumitrescu et al. | |
| 9,033,006 B2 * | 5/2015 | Perazzo | B65B 7/28 |
| | | | 141/319 |
| 10,807,743 B2 * | 10/2020 | Sisken | A61J 1/067 |

(Continued)

FOREIGN PATENT DOCUMENTS

| | | |
|---|---|---|
| DE | 19916662 A1 | 10/2000 |
| DE | 102016218126 A1 | 3/2018 |

(Continued)

*Primary Examiner* — Gloria R Weeks
(74) *Attorney, Agent, or Firm* — Knobbe, Martens, Olson & Bear, LLP

(57)     ABSTRACT

A machine for the preparation of a medical product with a worktop includes a hole for introducing syringes such that the injection points thereof are positioned for filling by the machine and a device for loading syringes. The device includes a fixed portion and a moveable portion, it being possible for the moveable portion to slide with respect to the fixed portion. The fixed portion includes housings for syringes that extend in a direction that is not parallel to that of the movement of the moveable portion. The moveable portion includes housings for syringes that extend in the direction of movement of the moveable portion. Two points of the movement of the moveable portion define a working position where the housings are aligned such that each pair of housings of the fixed portion and moveable portion receive the same syringe. The housings are misaligned in the loading position.

16 Claims, 11 Drawing Sheets

(56) References Cited

U.S. PATENT DOCUMENTS

| | | | |
|---|---|---|---|
| 11,072,446 B2 * | 7/2021 | Werk | B65B 7/2821 |
| 11,260,400 B2 * | 3/2022 | Zhu | B03C 1/288 |
| 12,151,839 B2 * | 11/2024 | Lizari Illarramendi | A61M 5/008 |
| 2007/0095024 A1 * | 5/2007 | Neeper | B65B 7/2821 |
| | | | 53/381.4 |
| 2007/0125442 A1 * | 6/2007 | Tribble | B65B 7/2821 |
| | | | 141/27 |
| 2014/0197120 A1 | 7/2014 | Seiwell | |
| 2016/0152359 A1 * | 6/2016 | Fontana | B65B 3/003 |
| | | | 53/411 |
| 2017/0144782 A1 | 5/2017 | Sisken et al. | |
| 2021/0170092 A1 * | 6/2021 | Zhou | A61M 5/008 |
| 2021/0309398 A1 * | 10/2021 | Kircher | B65B 67/1233 |
| 2024/0001040 A1 * | 1/2024 | Lizari Illarramendi | A61M 5/2033 |
| 2024/0399055 A1 * | 12/2024 | Matray | A61M 5/1408 |

FOREIGN PATENT DOCUMENTS

| | | | |
|---|---|---|---|
| ES | 2643119 B1 | 3/2018 | |
| JP | 2009-018879 A | 1/2009 | |

* cited by examiner

MACHINE FOR THE PREPARATION OF MEDICAL PRODUCT WITH DEVICE FOR LOADING SYRINGES OF MEDICAL PRODUCT

CROSS-REFERENCE TO RELATED APPLICATION

This application claims priority to European Patent Application No. 22382633.0 filed on Jul. 1, 2022, the disclosure of which including the specification, the drawings, and the claims is hereby incorporated by reference in its entirety.

FIELD OF THE INVENTION

The present application relates to a machine for the preparation of medical product, specifically to a machine with a device for loading syringes of medical product in said machine.

BACKGROUND OF THE INVENTION

Automated machines for the preparation of medical product, such as intravenous medication, for example, and for filling or loading medical containers, in other words containers with a medical product, are known. An example of such machines are dosing machines. These types of machines or devices are usually made up of a laminar flow cabinet and robotic means in the interior thereof which perform the necessary movements for removing medicine from a source container and injecting said medicine into end medical containers. The medical product is injected into the medical containers through an injection or dosing point located on the medical container.

These machines may comprise a worktop with holes for introducing the dosing points of the medical containers. Once introduced, the robotic means of the machine fill the various medical containers by introducing the medical product into a dosing point of the container. In this type of dosing machine with a worktop, the robotic means for filling containers are located inside the machine, beneath the worktop and arranged under the containers so that the dosing point of the medical container is positioned beneath the worktop. Other types of dosing machine may use safety barriers which separate the load from the robotic means without using a worktop.

Syringes usually comprise a plunger and a body, also known as a barrel. Said syringes comprise an injection or dosing point at one end of the syringe. This dosing point may be of the Luer-Lock type. The body of the syringe comprises a support tab. Said tab is also known as a flange. The plunger also has a base.

Dosing machines are usually designed for filling only a specific type of medical container and comprise supports for that type of container. Machines are known which allow various types of end medical containers to be supported by the use of specific adaptors for each type of container (syringes, bags, vials, bottles, infusers, cassettes, etc.). Said adaptors must be introduced into each adaptor support before beginning a preparation batch. Spanish patent document ES2643119 B1 discloses an example of an adaptor and a support for a dosing machine. Said supports help ensure that the dosing point of the containers is always in the same position, allowing easy automation of the dosing process.

A normal syringe loading process consists of removing the syringe adaptors from the fixed supports of the machine, introducing the syringes into the adaptors and then placing the adaptors, with the syringes therein, back into the supports of the machine. Because the syringes must be firmly secured in order to resist the filling operations of the machine, the means for fastening the syringes require the operator to apply considerable force to secure the syringes, normally to overcome the initial force of push-fitting elements. This is dangerous. Another problem with medical product preparation machines that have a worktop is that the process of loading syringes into the machine for filling is slow. This problem is even more relevant when loading a batch of containers, as the syringes must be placed in the adaptors one by one.

SUMMARY OF THE INVENTION

An object of the present invention is to disclose a machine for preparing medical product with a worktop which allows syringes to be loaded into the machine quickly and conveniently.

According to a first aspect, a machine for preparing medical product is disclosed, said machine comprising a worktop for introducing containers, said worktop comprising at least one hole for introducing syringes such that the injection points of the syringes are in a suitable position for filling by the machine and a device for loading said syringes. Said device comprises a fixed portion and a moveable portion, it being possible for the moveable portion to slide with respect to the fixed portion in a direction that is in a plane parallel to that of the worktop, said fixed portion comprising at least one series of housings for syringes in the form of recesses which extend in a direction that is not parallel to that of the movement of the moveable portion. The moveable portion comprises a series of housings for syringes which extend as recesses in the direction of movement of the moveable portion. Two distinct points of the movement of the moveable portion define a loading position and a working position respectively, such that, in the working position, said housings of the moveable portion are aligned with said housings of the fixed portion in pairs along axes perpendicular to the plane of movement of the moveable portion, such that each pair of housings of the fixed portion and of the moveable portion receive the same syringe. However, said pairs are misaligned in the loading position.

In said machine, the syringes are held by two different sets of housings which extend as recesses in non-parallel directions. This allows firm fixing without the operator having to apply substantial force. To allow positioning, the device has housings distributed on a fixed portion and a moveable portion. The syringes may be introduced into the housings of the fixed portion in an introduction direction, whereas the second set of housings is located in the moveable portion, and it is the movement of the moveable portion that causes the housings of the moveable portion to surround the syringe. Removing the syringes from the housings of the moveable portion would require a movement of the syringes in the introduction direction, but as the housings of the fixed portion extend in a position that is not parallel, this prevents their removal, and vice versa. Preferably, both sets of recesses (of the fixed portion and of the moveable portion) surround the main body of the syringes.

According to a preferred embodiment, the housings of the fixed portion are arranged in parallel, the housings of the moveable portion are arranged in series, in the direction of movement of the moveable portion.

Preferably, the recesses of the fixed portion extend in a direction perpendicular to the direction of movement of the moveable portion. In other words, the non-parallel direction is perpendicular. Locking is therefore maximal.

According to the present invention, the device may be removable, preferably having means for the positioning and removal thereof on the worktop.

Preferably, the moveable portion comprises a series of recesses and separation protrusions between said recesses, said syringe housings in the moveable portion being arranged on sides of said separation protrusions. This arrangement helps ensure that there is no interference between the fixed portion and the moveable portion during the syringe loading operation in the loading position.

Preferably, the fixed portion is situated between the worktop and the moveable portion.

Preferably, said housings do not have syringe retention elements that use push fitting by dimensional interference. There is therefore no need to apply force to introduce the syringes in the housings.

In an especially preferred embodiment, the present invention discloses a machine for the preparation of medical product. The machine comprises a worktop. The worktop comprises at least one opening, hole or cavity for introducing medical containers such that the injection points of the medical containers are in a suitable position for their filling by the machine. The machine comprises a removable device for loading syringes of medical product into the machine. Said removable device comprises a fixed portion and a moveable portion. The fixed portion comprises housings for syringes and separation protrusions between said housings. The tabs of the syringes being positioned above the fixed portion of the device when the syringes are arranged in the housings. The moveable portion of the device is a moveable head. The moveable portion comprises recesses for positioning syringes inside, separation protrusions between said recesses, and housings for syringes arranged on a side of said separation protrusions. The moveable portion of the device is preferably arranged above the fixed portion of the device. The moveable portion has the ability to move in a direction parallel to the fixed portion of the device, allowing the housings of the moveable portion to come in contact with syringes arranged in the housings of the fixed portion of the device, such that the tabs of the syringes arranged in the housings of the fixed portion are locked between the fixed portion and the moveable portion. The movement of the moveable portion defines an operating position and a loading position in the device. In the operating position, the housings of the moveable portion are aligned with the housings of the fixed portion (a position also referred to in this document as a closed position). In the loading position the device is positioned for loading syringes in said device and is a position in which the housings of the moveable portion are misaligned with the housings of the fixed portion (a position also referred to in this document as an open position).

The machine according to the present invention allows a batch of syringes to be positioned in the device and later for the device to be positioned in a machine for the preparation of medical product easily and quickly. First, the syringes are placed in the housings of the fixed portion of the device such that the dosing points of the syringes are oriented towards the machine for later filling. In this position, the tabs of the syringes are positioned above the fixed portion of the device. Next, the moveable portion is moved into a closed position to fasten the syringes.

Owing to the movement of the moveable portion of the device, in the closed position, the moveable portion is preferably positioned above the tab. This allows the moveable portion to act as a vertical stop to secure the syringes, the tabs of the syringes being positioned between the fixed portion and the moveable portion of the device, slowing the vertical movement of the tabs. When the syringe is exposed to rotation caused by an upward force such as that produced by the robotic means of the machine during the filling of the syringes, the syringe finds a stop on the upper portion which helps fastening the syringe. Moreover, the moveable portion acts as a centring element for the syringes because contact with the housing of the moveable portion helps align the syringe between the housings of the moveable portion and the housings of the fixed portion, facilitating the correct positioning thereof in a hole of the machine for its filling.

This results in a reduction in the force applied by the operator when loading the material, and also a reduction in the level of concentration required by the operator to load the material correctly.

Preferably, the moveable portion is incorporated in the device, in other words, said moveable portion has means that allow the connection thereof to the fixed portion.

Preferably, the worktop comprises various openings, holes or cavities with means for introducing medical containers, more preferably arranged in different work lines. These openings, holes or cavities allow the dosing points of the containers to be positioned for filling with medical product using robotic and/or automatic means of the machine.

Preferably, the fixed portion of the device comprises an upper portion and a lower portion. Said upper and lower portions of the fixed portion each comprise housings for syringes. Said upper and lower portions may also comprise separation protrusions between the housings, the housings of the upper portion being aligned with the housings of the lower portion. Contact of the body of the syringes with the housings allows the lateral movement of the syringes to be limited. This configuration enhances clamping of the syringes as there are more housings and therefore more points of contact.

Preferably, the device comprises elements for fixing to the machine arranged on the lower portion thereof.

Preferably, the machine comprises an anti-rotation system for the syringes placed in the housings. During filling of the containers, the robotic means of the machine apply force to the container. This force causes the syringes to rotate, and may even displace said syringes such that filling is difficult. The anti-rotation system limits this rotation and allows better fastening of the syringe to prevent or minimise the movement thereof in order to minimise any filling error.

Preferably, the anti-rotation system comprises support surfaces for the syringe tabs that are conjugate with the shape of said tabs. More preferably, said surfaces are positioned on respective steps arranged on the fixed portion of the device. Said step may also be a cavity or groove. Still more preferably, said surface is generally rectangular or U-shaped. The shape described above allows the surface and/or the step to act as an anti-rotation to prevent rotation caused by the machine. During filling of the syringe by the machine, the syringe tends to rotate. The presence of the step means that the syringe comes up against the wall thereof, said wall creating a stop that locks the tab of the syringe.

Preferably, the machine comprises second surfaces and/or second steps arranged in the housings of the moveable portion. The plunger of the syringe is usually pressed before filling to ensure there is no air initially in the empty syringe. Said second steps make it easier for the operator to visually identify that a check has been made to ensure the syringes are empty. If said check had not been made, the base of the plunger would jut out above the head. This second step may also be a groove or cavity.

Preferably, the device comprises a system for locking the device in the working position and/or in the operating position. In a preferred embodiment, the system for locking in the operating position comprises a shaft and elastic elements to recover the contact position with said shaft. Said elastic means are preferably a spring. The shaft is arranged above the spring such that extending the spring allows vertical movement of the shaft. The shaft and the spring are arranged in a housing of the fixed portion of the device. Preferably, said housing is situated on a side or on the handle of the fixed portion of the device, and is perpendicular to the direction of movement between the fixed portion and the moveable portion. The moveable portion of the device also comprises a through-hole. When, because of the movement, the through-hole and the shaft are aligned, owing to the action of the spring, the shaft penetrates, preferably in part, into the hole. This prevents movement of the moveable portion, causing the device to lock. This locking of the shaft allows the moveable portion or the moveable head to be fixed in the operating position of the machine, such that there is no unwanted movement of the moveable portion during the filling of the syringes, which could rupture the fastening of the syringes. More preferably, the moveable portion comprises a side wall, the hole for the shaft being arranged in said side wall of the moveable portion. Still more preferably, the locking system comprises a pusher or button arranged in the hole of the moveable portion. When the shaft extends, the pusher is extended, jutting out of the moveable portion. Actuation of the pusher compresses the spring and facilitates the unlocking of the shaft to again allow lateral movement of the moveable portion. This unlocking allows the moveable portion to return from the operating position to the container loading operation.

Preferably, the device comprises elastic means which, in the working position, apply a return force to raise the device to the loading position. Also preferably, the device comprises a guide with two stops, the ends of the guide corresponding to the loading position and the operating position of the device.

Preferably, the moveable portion of the device comprises claws for locking to the fixed portion of the device. These claws make it difficult for the moveable portion to be removed from the fixed portion of the device.

The present invention also discloses a method for loading syringes of medical product into a machine for the preparation of medical product which comprises the sequential steps of:

Placing the device in the syringe loading position,
Positioning the syringes in the housings of the fixed portion of the device,
Moving the moveable portion of the device in a direction parallel to the fixed portion of the device until the housings of the moveable portion come in contact with the syringes arranged in the housings of the fixed portion, such that the tabs of the syringes arranged in the housings of the fixed portion are locked between the fixed portion of the device and the moveable portion of the device.

As used in the present document, the term "medical container/s" refers to any type of container used in medicine for storing, preparing or administering medicines (for example, intravenous medicines such as non-cytostatic intravenous medicines including antibiotics and anaesthetics) and other solutions used in intravenous treatments (such as physiological solutions, saline solutions or nutritional solutions). The concept "medical product/s" is used in the present document to refer to these medicines and other solutions. The term "syringes of medical product" refers to syringes which are "medical containers".

As used in the present document, the term "dosing point/s" and "injection point/s" refer to the point of the medical container through which said medical container is dosed, in other words, the point through which the medicine (preferably intravenous medicines, such as non-cytostatic intravenous medicines including antibiotics and anaesthetics) or intravenous treatment solution (such as physiological solutions, saline solutions or nutritional solutions) is introduced into the medical container.

BRIEF DESCRIPTION OF THE DRAWINGS

For a better understanding, the accompanying drawings show an embodiment of the present invention given as an explanatory but non-limiting example.

DETAILED DESCRIPTION OF THE PREFERRED EMBODIMENTS

Figure 1:
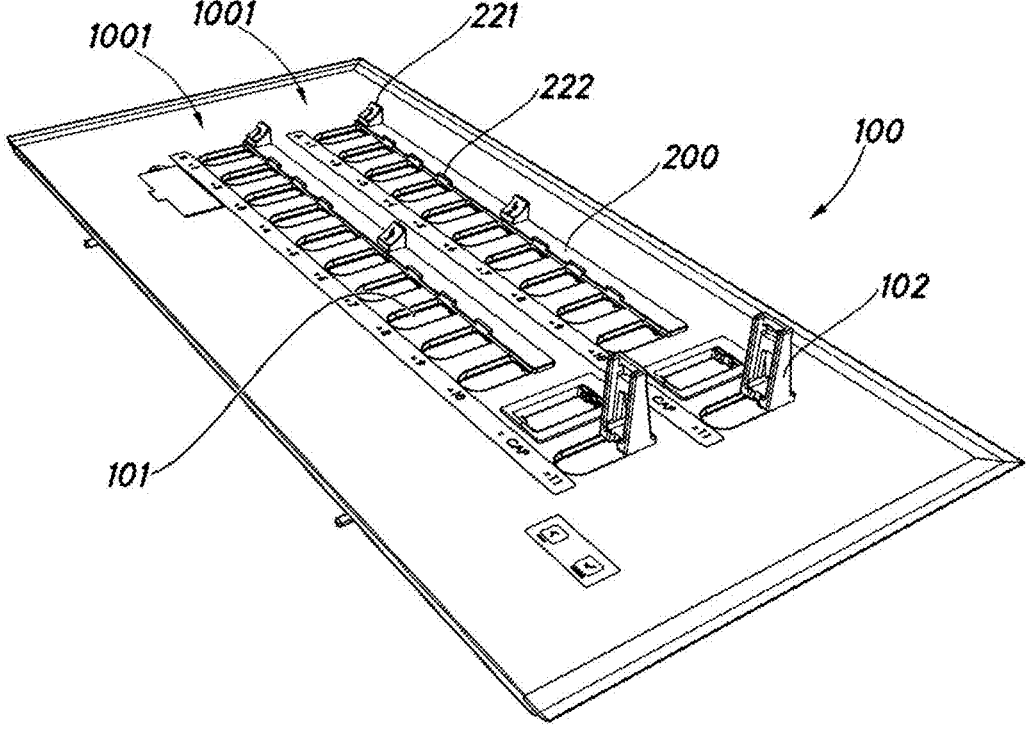
FIG. 1 shows an example of a worktop of a machine for the preparation of medical product according to the present invention.

FIG. 1 shows a worktop 100 of a machine 1000 for the preparation of medical products, specifically a worktop of a dosing machine which doses medical product into medical containers. Said worktop 100 is shown separated from the machine for illustrative purposes and it should be understood that said worktop forms part of the machine 1000 for the preparation of pharmaceutical products.

The worktop 100 comprises holes 101 for loading medical containers, more specifically for the introduction therein of the dosing points of medical containers, for example syringes. These holes may also be cavities. FIG. 1 shows a worktop 100 with two lines 1001 of holes 101, corresponding to two work lines 1001 of the machine 1000. Multiple lines allow various batches of containers to be filled at the same time. The machine may comprise a different number of work lines or a different number of holes in each line.

The worktop 100 of the machine comprises elongated supports 200 for fastening the device 3, one device for each work line 1001 of the machine. Each elongated support 200 comprises an actuator or retention element 221 and protruding teeth 222 for interconnection with the device 3. These protruding teeth 222 are positioned alternately along the elongated support 200. In the example shown, each elongated support 200 comprises two retention elements 221, allowing two loading devices 3 to be fastened on each support 200. This allows working with two batches of syringes in each work line 1001 of the machine. The retention elements 221 are shown positioned on the left side of the elongated support 200.

The holes 101 allow the introduction of individual supports 102 for adaptors for medical containers. The worktop 100 is shown with only two individual supports 102 for adaptors. These individual supports 102 are positioned at one end of the worktop 100, one for each work line 1001. In the embodiment, each support 102 allows a source container to be loaded. This source container may contain the medicine to be injected or dosed into the medical containers positioned in the holes or cavities of the worktop. Robotic means of the machine (not shown) remove the medicine from the source container and inject said medicine into the syringes. Furthermore, the rest of the holes 101 are shown without said individual supports 102 and have an elongate support 200 at the side thereof. According to the present invention, the loading device may be placed on the worktop 100 of the machine by fastening said loading device in the elongate supports 200 and the syringes can then be introduced into the device, such that the injection points of the syringes are beneath the worktop without the need for individual supports for each syringe. Alternatively, the device also allows the syringes to be positioned first in the device and then the device in the worktop.

FIGS. 2 to 10 show a device 3 for loading syringes into the machine according to a first embodiment of the present invention. The device is fastened on the worktop shown in FIG. 1 by means of the supports 200.

Figure 2:
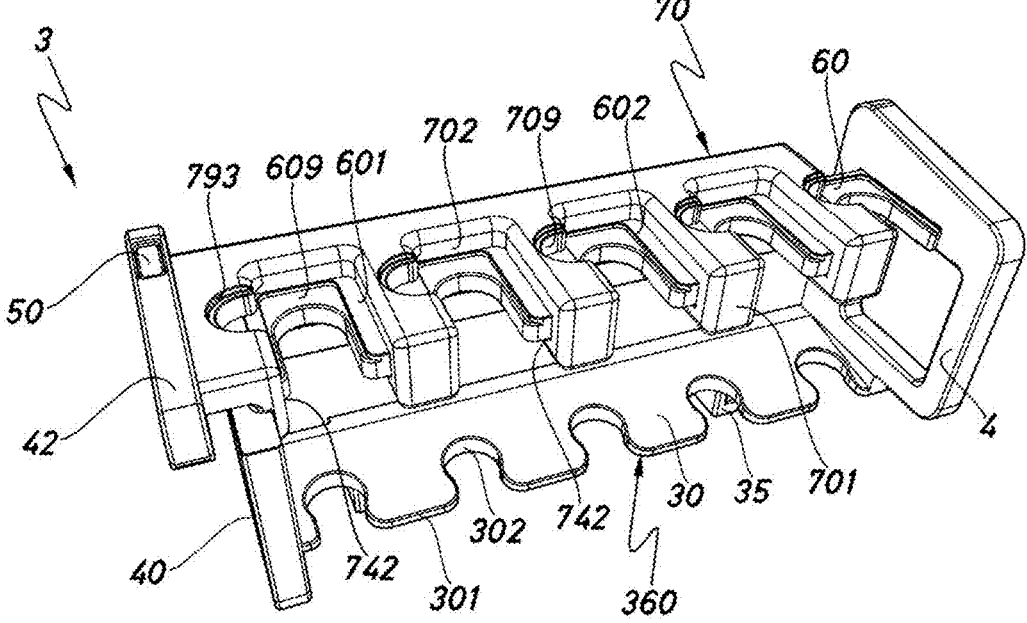
FIG. 2 is a perspective view of a device for loading syringes according to a first embodiment of the present invention, in the loading position and from the front face.
Figure 3:
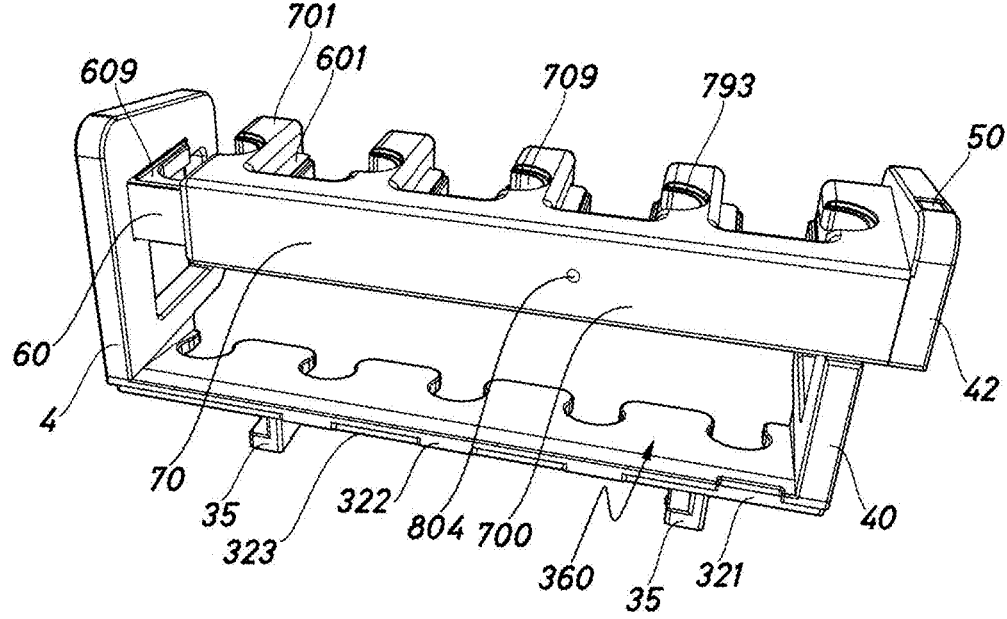
FIG. 3 is a perspective view of the device in FIG. 2 in the loading position and from the rear face.
Figure 4:
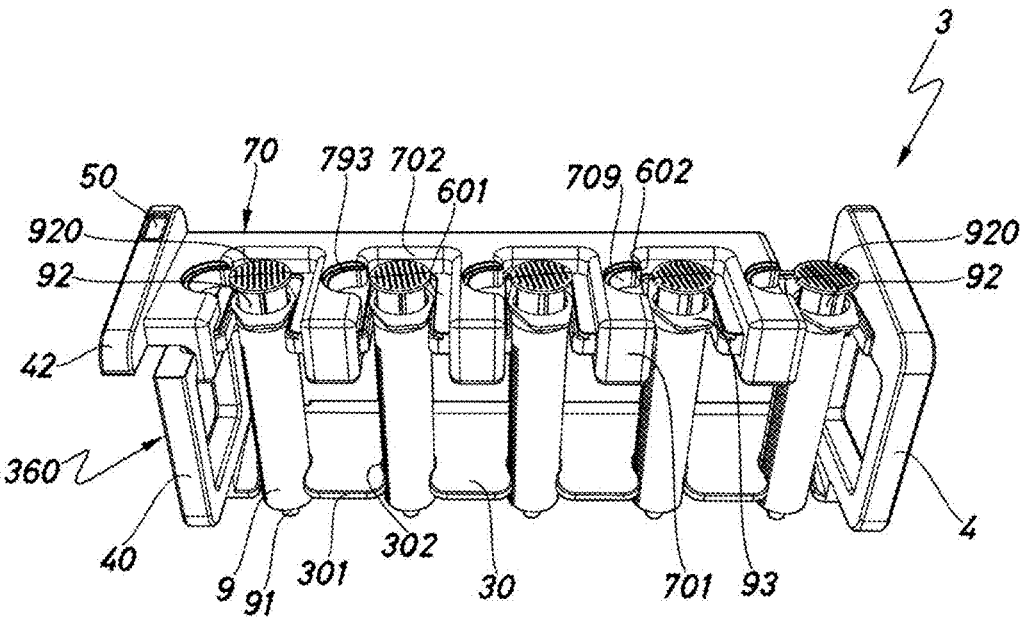
FIG. 4 is a perspective view of the device in FIG. 2 with the syringes introduced, in the loading position and from the front face.

FIGS. 2, 3 and 4 show the device in the loading position or open position. In other words, the position of the device for placing or loading medical containers therein. FIGS. 2 and 4 show the device from the front face whereas FIG. 3 shows the device from the rear face. In the context of this patent, the expression "rear" should be understood as the portion that is farthest from the operator who is performing the loading operations once the device is placed in the machine, whereas the "front" portion is the one that is closest to the operator during the operation of loading syringes into the machine.

The device 3 comprises a fixed portion 360, which in turn comprises a lower fixed portion 30 and an upper fixed portion 60. Both portions slide with respect to the other in a plane which, in the case in the example, is parallel to the worktop and a direction which, also in the example, is parallel to the work lines of the machine. The lower portion 30 and the upper portion 60 each comprise housings 302, 602 for housing syringes 9 and separation protrusions 301, 601 between said housings 302, 602. Each of the housings 302 of the lower portion 30 is aligned with a respective housing 602 of the upper portion 60. On placing a syringe 9 in the housing 602, the body of the syringe 9 is positioned inside the pair of housings 302-602. As can be seen in FIG.

4, the tab 93 is resting on the upper portion 60 of the device 3, and the dosing point 91 of the syringe is positioned beneath the lower portion 30 of the device 3 in order to facilitate the filling of the syringe 9 by the robotic means of the machine. The upper portion 60 also comprises first rectangular or U-shaped steps 609 with support surfaces for the tabs 93 of the syringes. The rectangular or U shape of the step 609 also serves as an anti-rotation system during the filling of the syringe, making difficult and/or preventing the rotation of the tab 93 and thus the rotation of the syringe 9.

The device 3 also comprises a portion 70 or head. The moveable portion 70 in the example is arranged above the upper portion 60 of the fixed portion 360 and is moveable in a direction parallel to the fixed portion 360. In other words, the moveable portion 70 can slide with respect to the fixed portion 360 in a plane parallel to the worktop 100 and/or to the lower portion 30 or base of the device 3. In addition, in the example the direction of movement is parallel to the work lines. Moreover, the direction of movement in the example is perpendicular to the introduction direction of the syringes into the housings 302, 602 of the fixed portion 360. The moveable portion 70 comprises recesses 702 for placing syringes inside, separation protrusions 701 between said recesses 702 and housings 709 for receiving the syringes. The recesses 702 extend in the same direction as the housings of the fixed portion 60. In the example, the housings 709 are arranged inside said recesses 702 of the moveable portion, on a side of the separation protrusions 701, which makes it easier for said housings to extend as recesses in the direction of movement of the moveable portion 70. Furthermore, the dimensions of the recesses 702 are greater than the dimensions of the housings 302, 602. The recesses 702 are aligned with each pair of housings 302-602 in the loading position of the device. The protrusions 701 comprise locking claws 742 at the ends thereof which receive conjugate portions of the fixed portion 360. These claws 742 are locked to the upper portion 60 of the device 3, preventing relative movements in directions other than the sliding direction between the fixed portion 360 and the moveable portion 70.

The housings 709 are semi-circular for receiving syringes, at least in part, the main body of the syringes. The lateral movement of the moveable portion 70 allows the housings 709 to move closer to the syringes 9, such that the syringes are housed simultaneously in the housings of the fixed portion 360 and of the moveable portion 70. This fastens the syringes, preventing said syringes from coming out, as the outward directions of the housings 709 of the moveable portion 70 do not coincide with the outward direction of the housings of the fixed portion. The edges of the housings 709 of the moveable portion 70 also comprise second steps 793 or rebates. These steps 793 make it easier to check that the syringes are empty before being filled.

The device 3 also comprises on its sides two side handles 4, 40. The moveable portion 70 comprises a side wall 42 on one of its sides. Said side wall 42 is aligned with the handle 40 of the device. The handles 4, 40 have the advantage of making it easier for an operator to grasp the device 3. In the embodiment shown, the side wall 42 of the moveable portion 70 is situated on the left of the device 3 once the device is placed on the worktop of the machine, the lateral movement of the moveable portion 70 being a leftward movement. Alternatively, the side wall 42 of the moveable portion may be situated on the right of the device and the lateral movement of the moveable portion 70 may be a rightward movement. The use of devices with both configurations makes it easier for the operator to load syringes by increasing the space available in the machine for moving the respective moveable portions 70.

The device 3 may comprise fastening elements to the rest of the machine for the preparation of containers of medical products, and in the particular case in the example, elements for fastening to the worktop 100 in FIG. 1. In the embodiment shown, these fastening elements are arranged on the lower portion 30 of the device 3. These fastening elements comprise protrusions 322, recesses 323, claws 35 and a groove 321. The recesses 323 are teeth intended to produce dimensional interference with conjugate elements of the machine, specifically with protrusions 222 of the elongate support 200 of the worktop 100 of the machine. These recesses 323 alternate with protrusions 322 along the lower portion 30 of the device 3. The claws 35 are L-shaped so as to allow the distal portion of the claw 35 to be beneath the worktop 100 after placing the device 3 on said worktop 100. This placing allows the claws 35 to produce dimensional interference with the lower portion of the worktop 100, preventing the upward movement of the device once the device 3 has been placed in the machine. The recess 321 (which in the example is in the form of a groove) allows a retention element 221 of the elongate support 200 of the machine to be introduced. The invention is not limited to these types of fastening elements and other known fastening elements may also be used.

Figure 5:
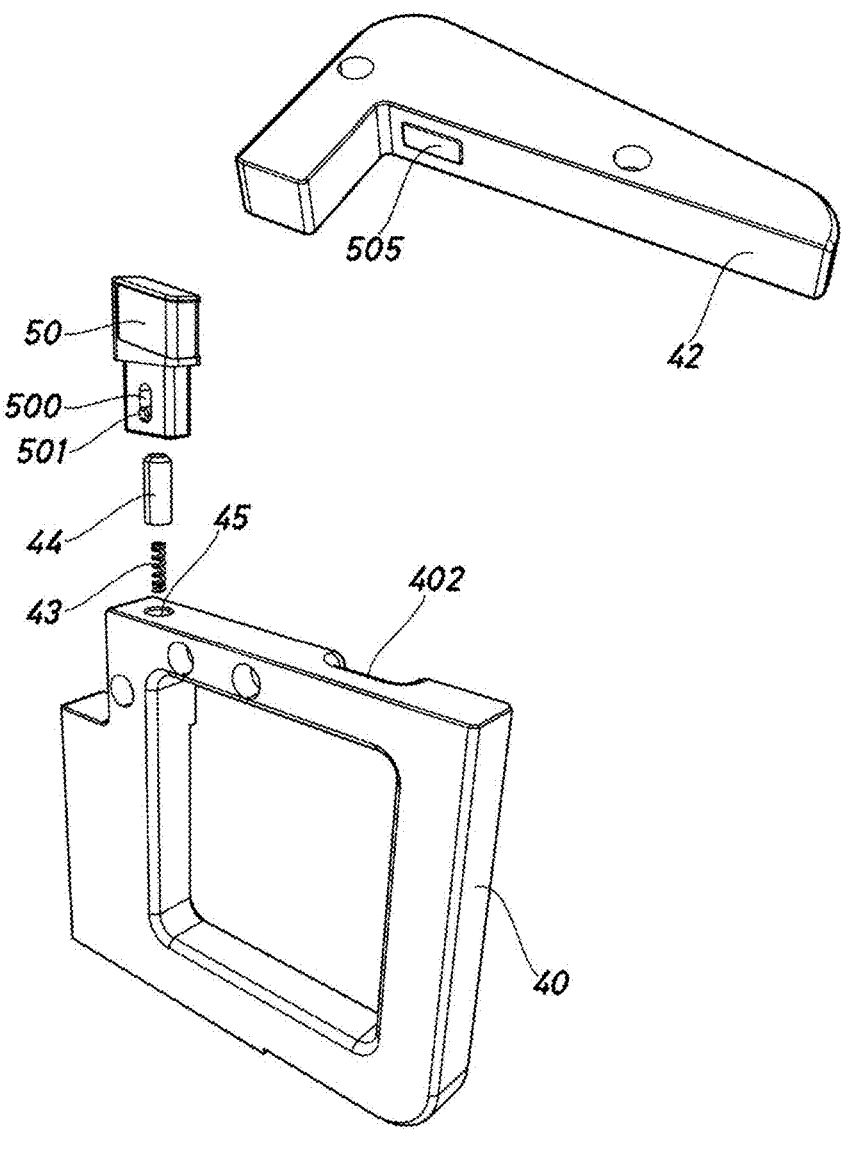
FIG. 5 is an exploded perspective view of the pusher, the handle of the fixed portion and the side wall of the moveable portion of the device.

FIG. 5 is an exploded view of the side wall 42 of the moveable portion 70 and the handle 40 of the device 3. FIG. 5 shows a hole 45 in the handle 40 of the fixed portion of the device. Arranged in said hole 45 are a shaft 44 and a spring 43. The spring is initially compressed in the hole 45 and the shaft 44 is arranged above the spring 43 such that extending the spring 43 allows the shaft 44 to move vertically. FIG. 5 also shows a through-hole 505 arranged in the side wall 42 of the moveable portion 70 of the device 3. The moveable portion 70 also comprises a pusher 50 arranged in the through-hole 505 of the side wall 42. Contact of the shaft 44 with the hole 505 of the moveable portion 70 allows the shaft 44 to move propelled by the spring 43, such that the shaft is introduced in part in the hole 505 of the moveable portion. The shaft 44 is then housed simultaneously in the hole 45 in the fixed portion and the hole 505 in the moveable portion 70, which prevents the relative movement of the moveable portion 70 of the device 3 with respect to the fixed portion 360. The pusher 50 also comprises a guide 500 with a fixed through-element 501, such that contact of the through-element 501 with the stops of the guide 500 limits the vertical movement of the pusher 50 along the hole 505.

In the loading position of the device, the moveable portion 70 is open for introducing the syringes into the device. In that position, the body of the moveable portion 70 is positioned on the shaft 44, blocking the outward movement of the shaft 44 and compressing the spring 43. Following the lateral movement of the moveable portion 70 of the device, the openings 45, 505 of the fixed and moveable portions are aligned. In that position, the spring 43 raises the shaft 44, the shaft 44 being introduced in part in the hole 505, which locks the device in the operating position. In said position, pressing the pusher 50 allows the shaft 44 to be compressed by compressing the pusher 50, which allows the shaft 44 to be positioned in the groove 45 of the handle 40, releasing the moveable portion 70 and allowing movement thereof from the operating position of the device 3 back to the loading position.

Figure 6:
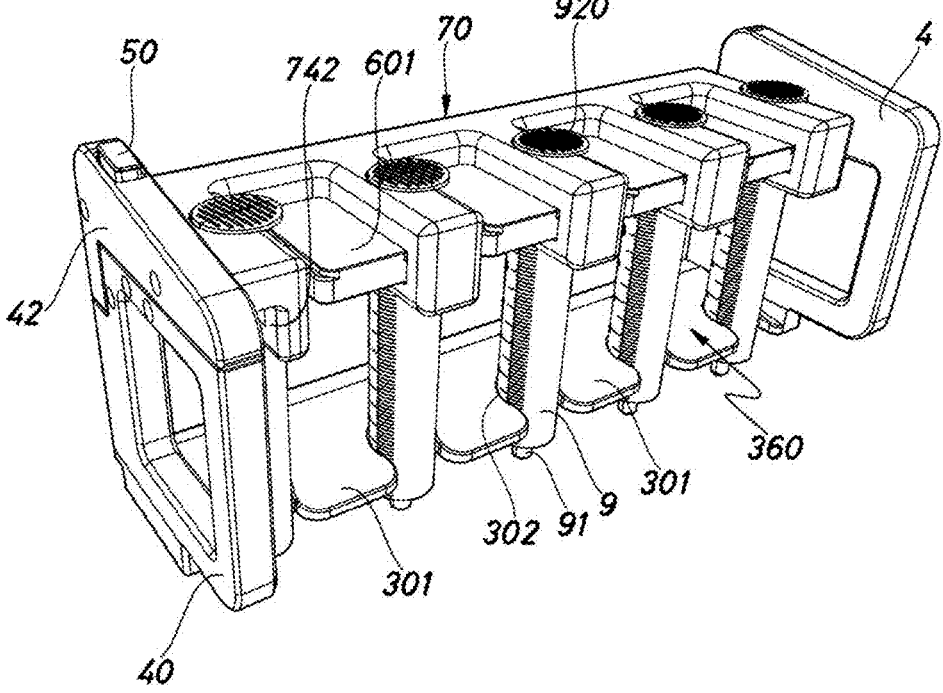
FIG. 6 is a perspective view of the device in FIG. 2 with the syringes introduced, in the operating position and from the front face.
Figure 7:
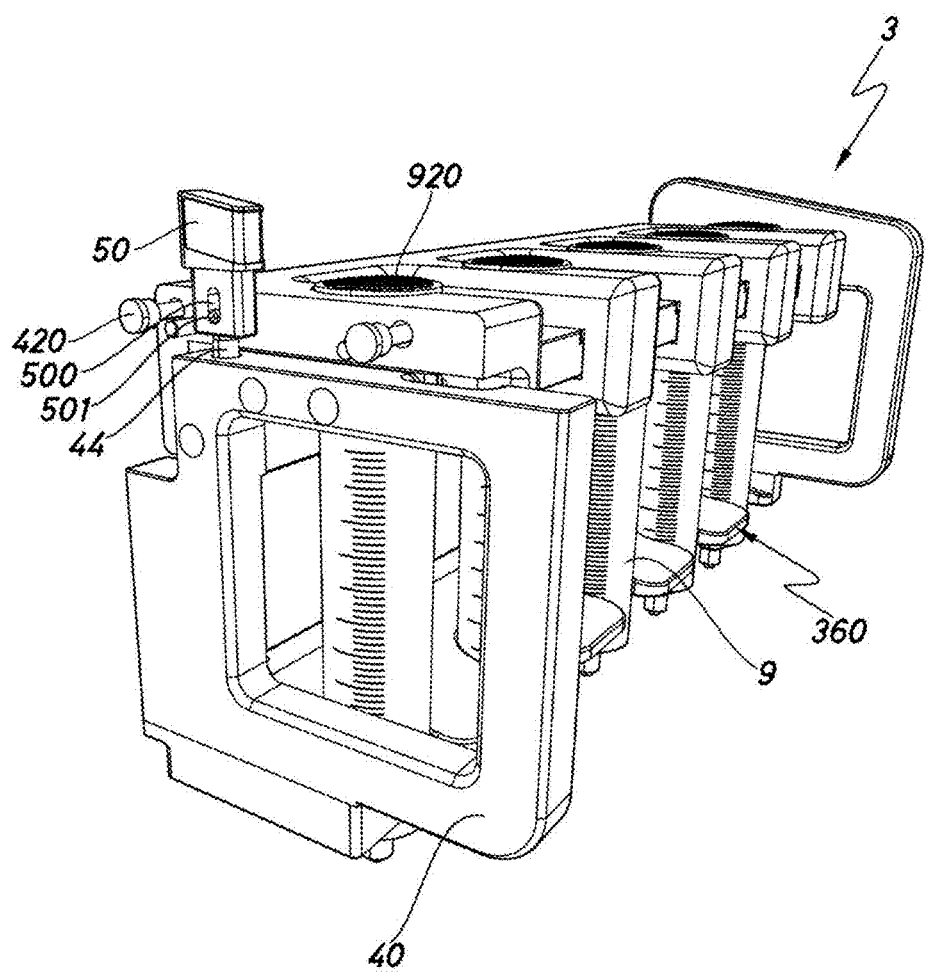
FIG. 7 is a perspective view of FIG. 6 of the moveable portion of the device.

FIGS. 6 and 7 show the device in the operating position. Previously, the syringes 9 were placed in the pairs of housings 302-602 in the device loading position and the moveable portion 70 was then moved laterally until the housings 709 were in contact with the syringes 9 or, at least, accommodating part of the main body thereof. In this operating position, the syringes are held by dimensional interference between the outward directions of the housings 709 of the moveable portion and the housings of the fixed portion 360. Moreover, in the example, the protrusions 601 of the fixed portion also interfere in the outward movement of the syringes from the housings 709 of the moveable portion. In addition, the protrusions 601 come in contact with the body of the syringes, fastening the syringes still further. FIG. 7 shows the device 3 in the same position as in FIG. 6, with the side wall 42 removed for illustrative purposes. As can be seen, in this position the pusher 50 is extended by the force applied by the shaft 44 and the spring 43, and juts out. The side wall 42 is connected to the head by fastening elements 420 such as by screwing.

Figure 8:
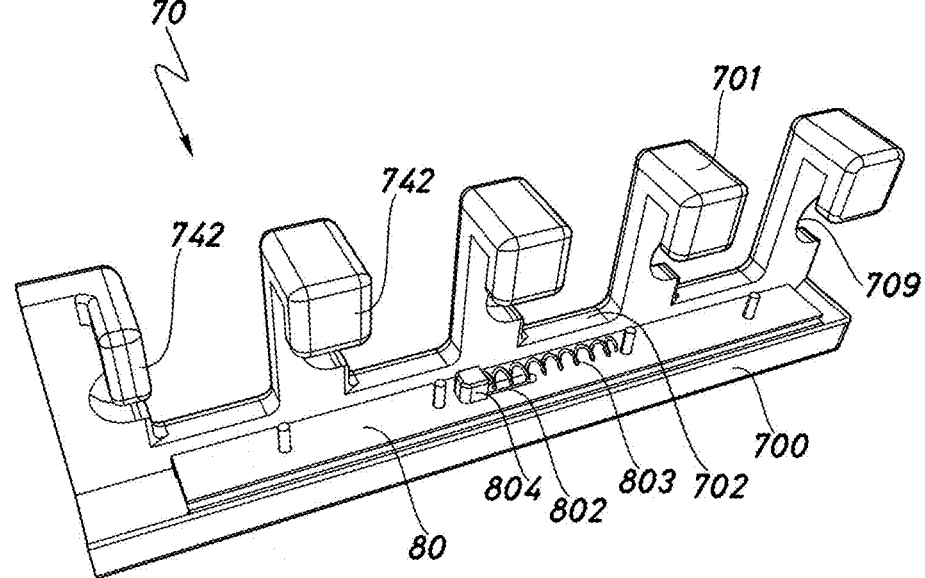
FIG. 8 is a perspective view of the moveable portion of the device.

FIG. 8 shows the moveable portion 70 without the side wall 42. In the perspective view, the interface area with the fixed portion can be seen. The moveable portion 70 comprises a platform 80 inside. This platform 80 is positioned between the rear portion 700 of the moveable portion 70 and the upper fixed portion 60 of the device. The platform is connected to the rear portion 700 of the moveable portion 70 by additional platforms 805 screwed to said rear portion 700 and by a through-element 804. The platform 80 also comprises a guide 802 and a spring 803. The spring is connected to the inner portion of the through-element 804. The through-element 804 is able to move along the guide 802. The guide 802 comprises two stops, and allows lateral movement of the moveable portion 70.

Figure 9:
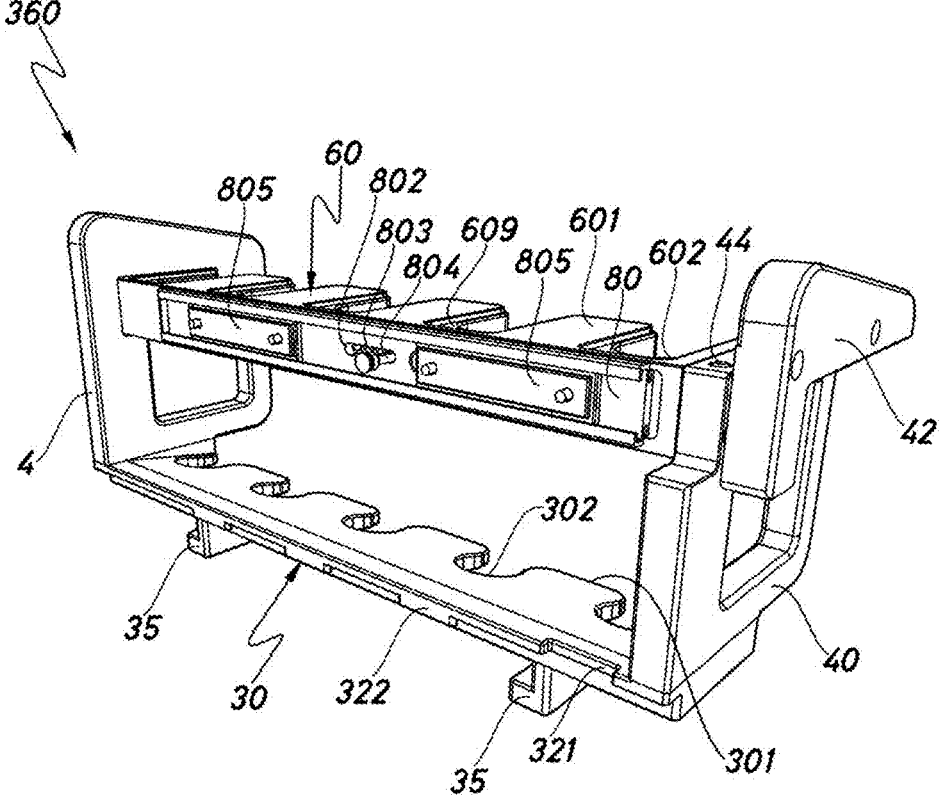
FIG. 9 is a perspective view of the device in the loading position and without the moveable portion.

FIG. 9 shows the device 3 in which the main body of the moveable portion, except for the platform the groove 802 and the spring 803, has been removed. During the lateral closing movement of the moveable portion 70, in other words, when moving from the device loading position to the device operating position, the moveable portion pulls the through-element 804, which causes the spring 803 to compress. When the device is unlocked by pressing the pusher 50, the spring 803 pushes the moveable portion to the loading or open position. In FIG. 9, it can also be seen that the upper portion 60 of the device 3 comprises housings 602 for the syringes, separated by recesses 601, also having a first step 609 to support syringe tabs 93.

Figure 10:
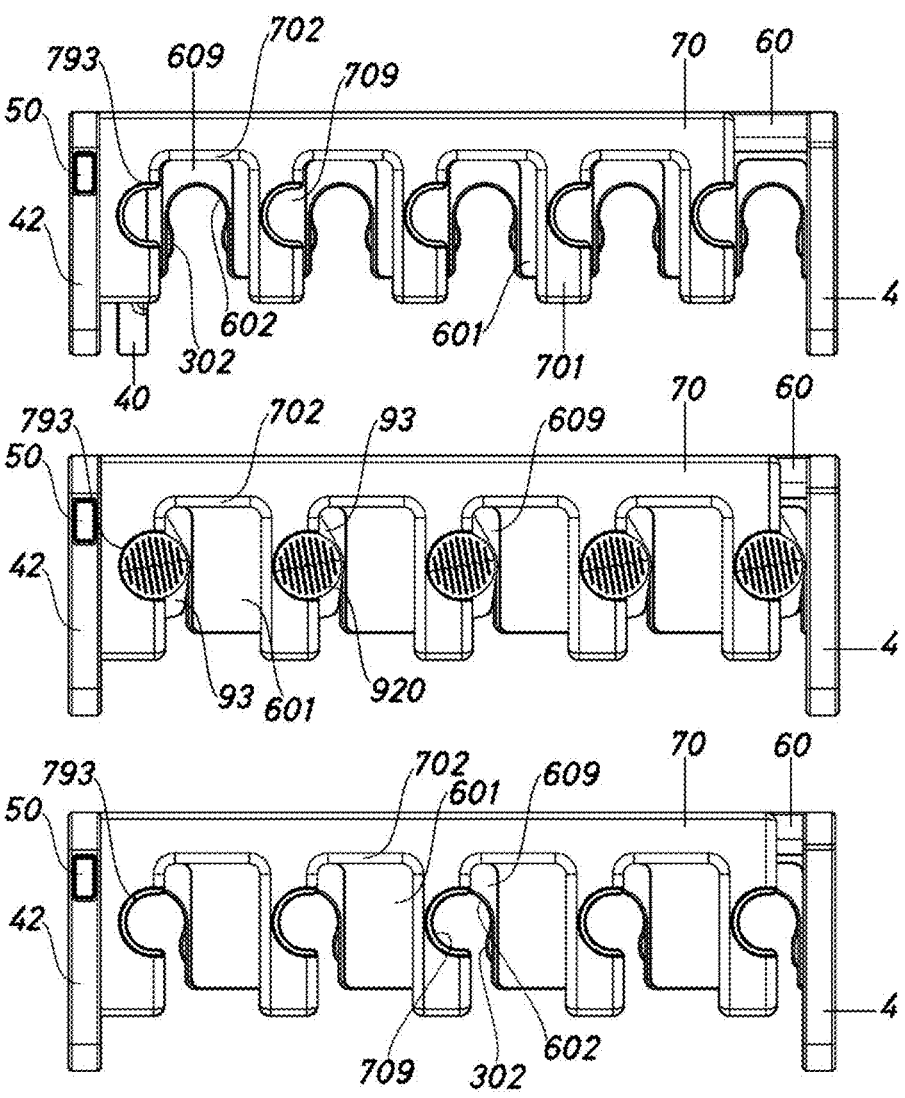
FIG. 10 shows three views from above of the worktop of the machine, with the device in the loading position, with the device in the closed position with the syringes introduced and with the device in the closed position without the syringes.

FIG. 10 shows three views from above of the device 3, a first in the device loading position (in which the moveable portion 70 is open) and two in the operating position (in which the moveable portion 70 is closed), one of said views with syringes 9 placed in the housings and the other without syringes 9.

The syringes 9 are loaded into the device 3 with the moveable portion 70 open, positioning the syringes 9 in the pair of housings 602-302 such that their tabs 93 are resting on the step 609 of the upper portion 60 of the device. Next, the moveable portion 70 is closed by moving said moveable portion laterally in the direction of the handle 4. During this lateral movement, the spring 803 of the moveable portion 70 is compressed. When the side wall 42 meets the handle the spring 43 of the shaft 44 of the handle 40 is positioned beneath the groove 505 of the button 50, expanding the shaft 44 which locks between the side wall 42 and the handle 40. Following this lateral movement, the device 3 is in the operating position. The syringes 9 are locked by dimensional interference between the semi-circular housings 709 for the syringes of the moveable portion 70 of the device 3 and the protrusions 601 of the fixed upper portion 60 of the device, making lateral movement thereof difficult.

After filling the syringes, said syringes can be removed by pressing the pusher 50, which in turn compresses the shaft 44 of the handle 40, which helps move the fixed portion 70 laterally from the operating position to the loading position owing to the spring 803, releasing the syringes to allow their removal.

The machine according to the invention therefore allows syringes to be loaded in the machine in batches, positioning the syringes in the housings of the device and locking the complete set of syringes all at the same time by a simple lateral movement of a moveable portion, without having to apply substantial force to lock the syringes.

Figure 11:
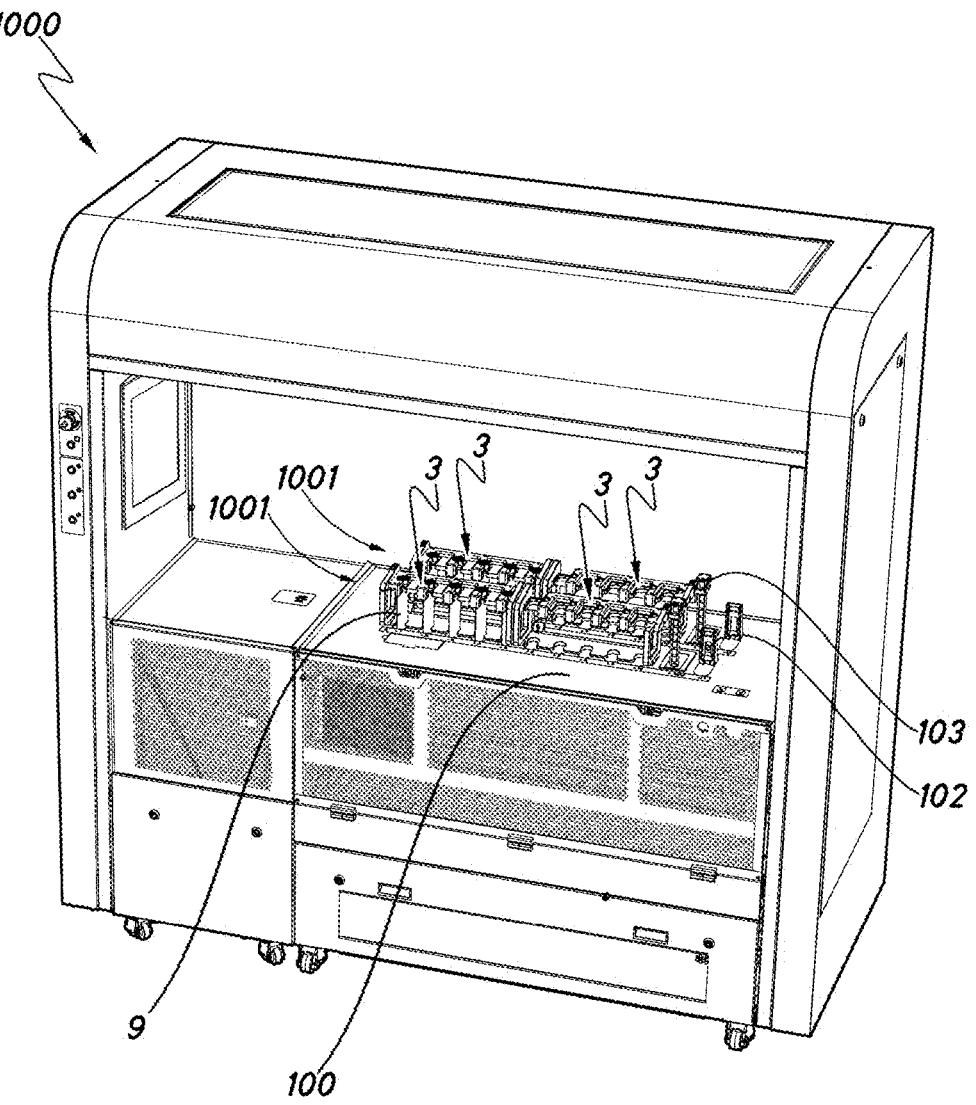
FIG. 11 is a perspective view of a machine for the preparation of medical products, with the device placed on the worktop of the machine.

FIG. 11 shows the machine 1000, with four devices 3 for loading syringes, placed on the worktop 100 of the machine 1000. In the figure, two work lines 1001 of the machine are shown, each of the two lines 1001 having two devices 3 placed in each of the elongated supports 200 of the worktop 100. The devices 3 positioned on the left of the worktop are devices of which the moveable portion is able to slide to the left, while the devices 3 positioned on the right of the worktop are devices of which the moveable portion is able to slide to the right. This configuration makes it easier to open the moveable portions once the devices 3 are placed on the worktop 100, which in turn facilitates the placing of syringes in the devices 3. The devices positioned on the left have been shown with syringes 9 placed therein. FIG. 13 also shows a dispenser 103 for syringe stoppers, arranged on the worktop 100.

Although the invention has been described and illustrated based on a representative example, it should be understood that said embodiment given as an example in no way limits the present invention, and therefore any variations included directly or by equivalence in the content of the accompanying claims should be considered included within the scope of the present invention.

What is claimed is:

1. A machine for preparation of medical products, said machine comprising:
a worktop with at least one hole for introduction therein of dosing points of containers and at least one work line configured to align such that the injection points of the containers in a position for filling by the machine; and
a device for loading said containers,
wherein said device comprises a fixed portion and a moveable portion, with two distinct points of movement of the moveable portion defining a loading position and a working position,
wherein the moveable portion is configured to slide with respect to the fixed portion in a direction parallel to said at least one work line that is in a plane parallel to a plane of the worktop,
wherein said fixed portion comprises at least one series of housings for receiving the containers in the form of recesses which extend in a direction which intersects with the direction that of the movement of the moveable portion,
wherein the moveable portion comprises recesses for placing the containers inside, housings, and separation protrusions, wherein each of the separation protrusions is positioned between each of said recesses of the moveable portion and each of said housings of the moveable portion,
wherein the recesses of the moveable portion extend in the same direction as the housings of the fixed portion, said housings of the moveable portion being arranged on a side of the separation protrusions and inside said recesses of the moveable portion, (i) such that, in the working position, said recesses of the moveable portion are aligned with said housings of the fixed portion in pairs along axes perpendicular to the plane of movement of the moveable portion, and such that each pair of the housings of the fixed portion and of the moveable portion is able to receive the same container, (ii) such that the housings of the fixed portion and the recesses of the moveable portion are not aligned in the loading position.

2. The machine according to claim 1, wherein the housings of the fixed portion are arranged in parallel, and wherein the housings of the moveable portion are arranged in series following the direction of movement of the moveable portion.

3. The machine according to claim 1, wherein the recesses of the fixed portion extend in a direction perpendicular to the direction of movement of the moveable portion.

4. The machine according to claim 1, wherein the moveable portion comprises a series of recesses and separation protrusions between said recesses, said syringe housings of the moveable portion being arranged on sides of said separation protrusions.

5. The machine according to claim 1, wherein the fixed portion is situated between the worktop and the moveable portion.

6. The machine according to claim 1, wherein the fixed portion of the device comprises an upper portion and a lower portion, said upper and lower portions of the fixed portion each comprising housings for containers and separation protrusions between the housings, the housings of the upper portion being aligned with the housings of the lower portion.

7. The machine according to claim 1, further comprising an anti-rotation system to prevent the movement of the syringes placed in the housings.

8. The machine according to claim 7, wherein the anti-rotation system comprises support surfaces for the syringe tabs, said support surfaces having a shape conjugate with said tabs.

9. The machine according to claim 1, further comprising a system for locking the device in the working position.

10. The machine according to claim 1, wherein the device comprises elastic means which, in the working position, apply a return force to lift the device to the loading position.

11. The machine according to claim 10, wherein the elastic means are situated in the moveable portion.

12. A method for loading the containers of the medical products into the machine according to claim 1 for the preparation of the medical products, comprising:
placing the device in the syringe-loading position of the containers;
positioning the containers in the housings of the fixed portion of the device; and
moving the moveable portion of the device in a direction parallel to the fixed portion until the housings of the moveable portion come in contact with the containers arranged in the housings of the fixed portion, such that tabs of the containers arranged in the housings of the fixed portion are locked between the fixed portion of the device and the moveable portion of the device.

13. The method according to claim 12, wherein the containers are syringes.

14. The machine according to claim 1, wherein the containers are syringes.

15. A machine for the preparation of medical product, said machine comprising
a worktop for introducing containers, said worktop comprising at least one hole for introducing syringes such that the injection points of the syringes are in a suitable position for filling by the machine and a device for loading said syringes, and a system for locking the device in the working position wherein said device comprises a fixed portion and a moveable portion, it being possible for the moveable portion to slide with respect to the fixed portion in a direction that is in a plane parallel to that of the worktop, said fixed portion comprising at least one series of housings for syringes in the form of recesses which extend in a direction that is not parallel to that of the movement of the moveable portion, and in that the moveable portion comprises a series of housings for syringes which extend as recesses in the direction of movement of the moveable portion, two distinct points of the movement of the moveable portion defining a loading position and a working position respectively, such that, in the working position, said housings of the moveable portion are aligned with said housings of the fixed portion in pairs along axes perpendicular to the plane of movement of the moveable portion, such that each pair of housings of the fixed portion and of the moveable portion can receive the same syringe, being misaligned in the loading position, wherein said locking system comprises a shaft and elastic elements for recovering a contact position with said shaft, the shaft and the elastic means being arranged in a housing of the fixed portion of the device and in that the moveable portion of the device comprises a hole, such that when the shaft of the fixed portion of the device is aligned with the hole of the moveable portion the shaft penetrates into the hole owing to the action of the elastic means, locking the device.

16. The machine according to claim 15, further comprising a pusher arranged in the hole of the moveable portion, actuation of which facilitates the unlocking of the device.

* * * * *